US00PP22883P2

(12) United States Plant Patent
Sakazaki

(10) Patent No.: US PP22,883 P2
(45) Date of Patent: Jul. 24, 2012

(54) ***PETUNIA* PLANT NAMED 'USTUN29801'**

(50) Latin Name: *Petunia×hybrida*
Varietal Denomination: USTUN29801

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 205 days.

(21) Appl. No.: 12/802,249

(22) Filed: Jun. 1, 2010

(51) Int. Cl.
*A01H 5/00* (2006.01)

(52) U.S. Cl. ..... Plt./356.2

(58) Field of Classification Search ..... Plt./356.2
See application file for complete search history.

*Primary Examiner* — Susan McCormick Ewoldt
(74) *Attorney, Agent, or Firm* — C. A. Whealy

(57) ABSTRACT

A new and distinct cultivar of *Petunia* plant named 'USTUN29801', characterized by its outwardly spreading and low mounding plant habit; freely branching and vigorous growth habit; early and freely flowering habit; small dark violet-colored flowers; and good garden performance.

1 Drawing Sheet

Botanical designation: *Petunia×hybrida.*
Cultivar denomination: 'USTUN29801'.

BACKGROUND OF THE INVENTION

The present invention relates to a new and distinct cultivar of *Petunia* plant, botanically known as *Petunia×hybrida* and hereinafter referred to by the name 'USTUN29801'.

The new *Petunia* plant is a product of a planned breeding program conducted by the Inventor in Hikone, Shiga, Japan and Bonsall, Calif. The objective of the breeding program is to create new *Petunia* plants with compact plant habit, freely branching growth habit, early flowering, attractive small flowers and good summer performance.

The new *Petunia* plant originated from a cross-pollination made by the Inventor on May 14, 2004 in Hikone, Shiga, Japan of *Petunia×hybrida* 'MP20', disclosed in U.S. Plant Pat. No. 12,857, as the female, or seed, parent with *Petunia×hybrida* 'Bluette Blue', not patented, as the male, or pollen, parent. The new *Petunia* plant was discovered and selected by the Inventor as a single flowering plant within the progeny of the stated cross-pollination in a controlled environment in Bonsall, Calif. on Jul. 17, 2007.

Asexual reproduction of the new *Petunia* plant by vegetative cuttings in a controlled greenhouse environment in Bonsall, Calif. since Jul. 20, 2007, has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'USTUN29801'. These characteristics in combination distinguish 'USTUN29801' as a new and distinct cultivar of *Petunia* plant:

1. Outwardly spreading and low mounding plant habit.
2. Freely branching and vigorous growth habit.
3. Early and freely flowering habit.

4. Small dark violet-colored flowers.
5. Good garden performance.

In side-by-side comparisons conducted in Bonsall, Calif., plants of the new *Petunia* differ from plants of the female parent, 'MP20', in the following characteristics:

1. Plants of the new *Petunia* are not as creeping as plants of 'MP20'.
2. Plants of the new *Petunia* have larger flowers than plants of 'MP20'.
3. Plants of the new *Petunia* and 'MP20' differ in flower color as plants of 'MP20' have lavender-colored flowers.

In side-by-side comparisons conducted in Bonsall, Calif., plants of the new *Petunia* differ from plants of the male parent, 'Bluette Blue', in the following characteristics:

1. Plants of the new *Petunia* are not as mounding as plants of 'Bluette Blue'.
2. Plants of the new *Petunia* and 'Bluette Blue' differ in flower color as plants of 'Bluette Blue' have dark blue-colored flowers.

Plants of the new *Petunia* can be compared to plants of 'Kakegawa S28', disclosed in U.S. Plant Pat. No. 13,887. In side-by-side comparisons conducted in Bonsall, Calif., plants of the new *Petunia* differed from plants of 'Kakegawa S28' in the following characteristics:

1. Plants of the new *Petunia* were stronger than and not as vigorous as plants of 'Kakegawa S28'.
2. Plants of the new *Petunia* had smaller flowers than plants of 'Kakegawa S28'.
3. Plants of the new *Petunia* and 'Kakegawa S28' differed in flower color as plants of 'Kakegawa S28' had dark purple-colored flowers.

Plants of the new *Petunia* can also be compared to plants of 'Conviolet', disclosed in U.S. Plant Pat. No. 13,510. In side-by-side comparisons, plants of the new *Petunia* differed from plants of 'Conviolet' in the following characteristics:

1. Plants of the new *Petunia* were smaller than plants of 'Conviolet'.
2. Plants of the new *Petunia* had smaller flowers than plants of 'Conviolet'.

3. Plants of the new *Petunia* and 'Conviolet' differed in flower color as plants of 'Conviolet' had dark purple-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet comprises a side perspective view of a typical plant of 'USTUN29801' grown in a container.

The photograph at the top of the sheet is a close-up view of a typical flowering plant of 'USTUN29801'.

DETAILED BOTANICAL DESCRIPTION

The aforementioned photographs and following observations, measurements and values describe plants grown during the spring in 15-cm containers in an outdoor nursery in Bonsall, Calif. During the production of the plants, day temperatures ranged from 18° C. to 24° C., night temperatures ranged from 5° C. to 8° C. and light levels ranged from 7,000 to 10,000 foot-candles. Plants were pinched one time and were eleven weeks old when the photographs and description were taken. In the following description, color references are made to The Royal Horticultural Society Colour Chart, 2007 Edition, except where general terms of ordinary dictionary significance are used.

Botanical classification: *Petunia×hybrida* 'USTUN29801'.

Parentage:

*Female, or seed, parent.*—*Petunia×hybrida* 'MP20', disclosed in U.S. Plant Pat. No. 12,857.

*Male, or pollen, parent.*—*Petunia×hybrida* 'Bluette Blue', not patented.

Propagation:

*Type*.—Terminal vegetative cuttings.

*Time to initiate roots, summer*.—About three days at temperatures ranging from 17° C. to 29° C.

*Time to initiate roots, winter*.—About four days at temperatures ranging from 17° C. to 21° C.

*Time to produce a rooted plant, summer*.—About 15 days at temperatures ranging from 17° C. to 29° C.

*Time to produce a rooted plant, winter*.—About 20 days at temperatures ranging from 17° C. to 21° C.

*Root description*.—Medium in thickness, fibrous; white in color.

*Rooting habit*.—Freely branching; moderately dense.

Plant description:

*Plant and growth habit*.—Annual flowering plant; outwardly spreading and low mounding plant habit; vigorous growth habit; freely branching habit with about six to seven primary lateral branches and numerous secondary lateral branches per plant; pinching enhances development of lateral branches; dense and bushy habit.

*Plant height*.—About 16 cm.

*Plant diameter* (*area of spread*).—About 60 cm.

*Lateral branches*.—Length: About 32 cm. Diameter: About 2 mm. Internode length: About 1.5 cm to 2.5 cm. Strength: Strong. Texture: Pubescent; viscid, glandular. Color: Close to 144A.

Foliage description:

*Arrangement*.—Alternate before flowering; opposite after flowers develop; simple.

*Length*.—About 3.8 cm.

*Width*.—About 2.4 cm.

*Shape*.—Elliptical.

*Apex*.—Acute.

*Base*.—Attenuate.

*Margin*.—Entire.

*Texture, upper and lower surfaces*.—Pubescent; viscid.

*Venation pattern*.—Pinnate, arcuate.

*Color*.—Developing leaves, upper surface: Close to 146A. Developing leaves, lower surface: Close to 146B. Fully expanded leaves, upper surface: Close to 147A; venation, close to 146B. Fully expanded leaves, lower surface: Close to 147B; venation, close to 146B.

*Petioles*.—Length: About 1 cm. Diameter: About 2 mm. Texture, upper and lower surfaces: Pubescent; glandular. Color, upper and lower surfaces: Close to 146C.

Flower description:

*Flower type and habit*.—Single axillary salverform flowers; flowers face mostly upward or outward; freely flowering habit, about 55 flower buds and open flowers per lateral branch.

*Natural flowering season*.—Long day responsive; long flowering period, plants flower from early spring until frost in the autumn, flowering continuous during this period; early flowering habit, plants begin flowering about six weeks after planting.

*Flower longevity on the plant*.—About three to five days; flowers persistent.

*Fragrance*.—Sweet with a hint of vanilla.

*Flower size*.—Diameter: About 3.4 cm. Depth (height): About 3.2 cm. Tube length: About 2.6 cm. Throat diameter, distal end: About 9 mm. Tube diameter, proximal end: About 4 mm.

*Flower buds*.—Length: About 2.9 cm. Diameter: About 5 mm. Shape: Elongated oblong. Color: Close to N187C.

*Petals*.—Quantity/arrangement: About five petals fused in a single whorl, funnelform. Petal lobe length (from throat): About 1.8 cm. Petal lobe width: About 1.7 cm. Petal lobe shape: Roughly fan-shaped. Petal lobe apex: Acute or slightly mucronate. Petal lobe margin: Entire. Petal lobe texture, upper and lower surfaces: Smooth, glabrous; velvety. Throat texture: Smooth, glabrous. Tube texture: Pubescent; viscid. Color: When opening, upper surface: Close to 86A. When opening, lower surface: More grey than 79D. Fully opened, upper surface: Brighter than 86A; venation, close to N92B; color becomes closer to 83B to 83C with development. Fully opened, lower surface: Close to 86B; venation, close to N92A; color does not fade with development. Flower throat: Close to 79B; venation, close to N92B. Flower tube (outside): Close to 83A; venation, close to N92A.

*Sepals*.—Arrangement/appearance: Single whorl of five sepals fused at base, star-shaped calyx. Length: About 1.6 cm. Width: About 2 mm. Shape: Lanceolate. Apex: Acute to rounded. Margin: Entire. Texture, upper and lower surfaces: Pubescent. Color, upper and lower surfaces: Close to 146B.

*Peduncles*.—Length: About 2 cm. Width: About 1 mm. Angle: About 45° to 60° from the stem axis. Strength: Moderately strong. Texture: Pubescent. Color: Close to 146B.

*Reproductive organs*.—Stamens: Quantity per flower: Five. Filament length: About 1.7 cm. Filament color: Close to 91C. Anther shape: Oval. Anther length: About 2 mm. Anther color: Close to 90A. Pollen amount: Moderate. Pollen color: Close to 93B. Pistils: Quantity per flower: One. Pistil length: About 1.7 cm. Style length: About 1.4 cm. Style color: Close to 147C. Stigma shape: Rounded anvil-shaped. Stigma color: Close to N189B. Ovary color: Close to 146D.

*Seed/fruit*.—Seed and/or fruit production has not been observed.

Pathogen/pest resistance: Plants of the new *Petunia* have not been noted to be resistant to pathogens or pests common to *Petunia*.

Garden performance: Plants of the new *Petunia* have been observed to have good garden and summer performance and have been observed to tolerate rain, wind and temperatures ranging from about 1° C. to about 40° C.

It is claimed:

1. A new and distinct *Petunia* plant named 'USTUN29801' as illustrated and described.

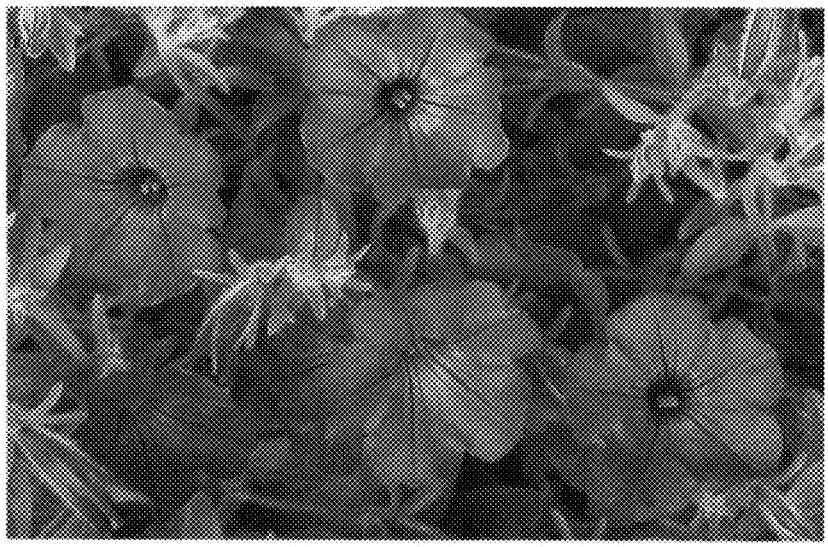
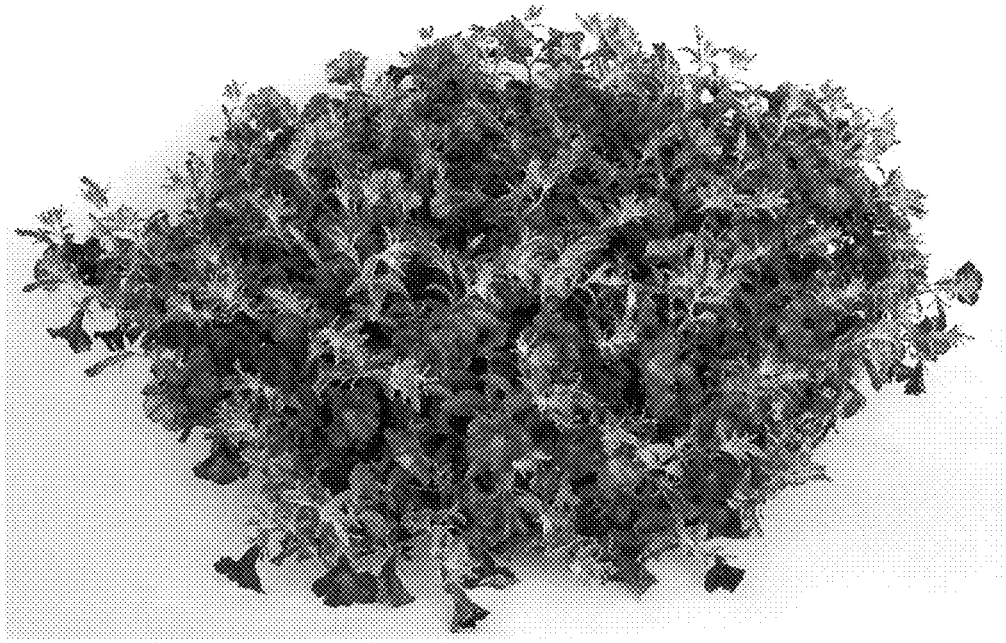

* * * * *